(12) United States Patent
Farrell et al.

(10) Patent No.: US 12,365,885 B2
(45) Date of Patent: Jul. 22, 2025

(54) PRODUCTION OF RIBOFLAVIN

(71) Applicant: DSM IP ASSETS B.V., Heerlen (NL)

(72) Inventors: Christopher Mark Farrell, Kaiseraugst (CH); Sébastien Eric Potot, Kaiseraugst (CH); Zoltán Prágai, Kaiseraugst (CH); Michael Patrick Anaya, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 409 days.

(21) Appl. No.: 17/293,800

(22) PCT Filed: Nov. 11, 2019

(86) PCT No.: PCT/EP2019/080835
§ 371 (c)(1),
(2) Date: May 13, 2021

(87) PCT Pub. No.: WO2020/099303
PCT Pub. Date: May 22, 2020

(65) Prior Publication Data
US 2022/0010291 A1    Jan. 13, 2022

Related U.S. Application Data

(60) Provisional application No. 62/767,612, filed on Nov. 15, 2018.

(51) Int. Cl.
*C12N 9/16* (2006.01)
*C12P 17/16* (2006.01)

(52) U.S. Cl.
CPC .............. *C12N 9/16* (2013.01); *C12P 17/165* (2013.01); *C12Y 301/03074* (2013.01)

(58) Field of Classification Search
CPC ......... C12N 9/16; C12N 15/52; C12P 17/165; C12P 25/00; C12Y 301/03074
See application file for complete search history.

(56) References Cited

U.S. PATENT DOCUMENTS

| 5,837,528 | A | 11/1998 | Perkins et al. | |
|---|---|---|---|---|
| 7,022,524 | B1 | 4/2006 | Phillips et al. | |
| 7,022,527 | B2 | 4/2006 | Phillips et al. | |
| 7,598,066 | B2 * | 10/2009 | Hoshino | C12N 9/16 435/254.2 |
| 2006/0263862 | A1 | 11/2006 | Hoshino et al. | |

FOREIGN PATENT DOCUMENTS

| CN | 102209780 | | 10/2011 |
|---|---|---|---|
| CN | 102245781 | | 11/2011 |
| EP | 0 405 370 | | 1/1991 |
| EP | 1 186 664 | | 3/2002 |
| EP | 2 000 477 | | 12/2008 |
| EP | 2186880 | A1 | 5/2010 |
| IN | 4290/DELNP/2011 | A | 4/2012 |
| JP | 2002253243 | A | 9/2002 |
| WO | 2004/113510 | | 12/2004 |
| WO | 2006/077258 | | 7/2006 |
| WO | 2007/051552 | | 5/2007 |
| WO | 2008/000632 | | 1/2008 |
| WO | 2010/052319 | | 5/2010 |
| WO | 2017/036903 | | 3/2017 |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
Phan et al., Heterologous Gene Expression in *E. coli* Methods and Protocols, Methods in Molecular Biology vol. 1586, chapter 21, pp. 325-334, published online May 4, 2017.*
Sousa et al., Microbiology 148(Pt5): 1291-1303, 2002.*
Capela et al., GenBank accession No. CAC41872 Mar. 7, 2015.*
International Search Report for PCT/EP2019/080835 dated Feb. 28, 2020, 3 pages.
Written Opinion of the ISA for PCT/EP2019/080835 dated Feb. 28, 2020, 5 pages.
Altschul et al, "Basic Local Alignment Search Tool," J. Mol. Biol. (1990) 215, 403-410.
Altschul et al., "Gapped BLAST and PSI-BLAST: a new generation of protein database search programs," Nucleic Acids Research, 1997, vol. 25, No. 17, 3389-3402.
Bretzel et al, "Commercial riboflavin production by recombinant *Bacillus subtilis*: down-stream processing and comparison of the composition of riboflavin produced by fermentation or chemical synthesis," Journal of Industrial Microbiology & Biotechnology (1999) 22, 19-26.
Kil et al; Riboflavin operon of *Bacillus subtilis*: unusual symmetric arrangement of the regulatory region, Mol Gen Genet (1992) 233: 483-486.
Mack et al, "Regulation of Riboflavin Biosynthesis in Bacillus subtilis is Affected by the Activity of the Flavokinase/Flavin Adenine Dinucleotide Synthetase Encoded byribC" *J. Bacteriol.*, (1998), 180(4):950.
Needleman et al., "A General Method Applicable to the Search for Similarities in the AMINO Acid Sequence of Two Proteins," *J. Mol. Biol.* (1970) 48, 443-453.
Perkins et al, "Genetic engineering of *Bacillus subtilis* for the commercial production of riboflavin," Journal of Industrial Microbiology & Biotechnology (1999) 22, 8-18.

(Continued)

*Primary Examiner* — Delia M Ramirez
(74) *Attorney, Agent, or Firm* — Nixon & Vanderhye P.C.

(57) ABSTRACT

The present invention is related to an improved process for production of vitamin B2 using a genetically engineered host cell comprising a heterologous enzyme with pyridoxal phosphatase activity. Using said modified host cell, the yield of riboflavin production could be increased by at least about 5%.

12 Claims, 2 Drawing Sheets
Specification includes a Sequence Listing.

(56) References Cited

OTHER PUBLICATIONS

Rice_et al, "EMBOSS: The European Molecular Biology Open Software Suite," The European Molecular Biology Open Software Suite, TIG Jun. 2000, vol. 16, No. 6, 276-277.
Sambrook et al, "Molecular Cloning," A Laboratory Manual Second Edition, Cold Spring Harbor Laboratory Press 1989.
Sarge et al, "Catalysis of an Essential Step in Vitamin $B_2$ Biosynthesis by a Consortium of Broad Spectrum Hydrolases," ChemBioChem 2015, 16, 2466-2469.
Ullmann's Encyclopedia of Industrial Chemistry Thorium and Thorium Compounds to Vitamins, vol. A27, 514-517.
Lin et al., "Metabolic engineering of *Escherichia coli* for the production of riboflavin", Microbial Cell Factories, 13:104, 12 pages (2014).

* cited by examiner

PRODUCTION OF RIBOFLAVIN

CROSS-REFERENCE TO RELATED APPLICATIONS

This application is the U.S. national phase of International Application No. PCT/EP2019/080835 filed Nov. 11, 2019 which designated the U.S. and claims priority to U.S. Provisional Application No. 62/767,612 filed Nov. 15, 2018, the entire contents of each of which are hereby incorporated by reference.

REFERENCE TO SEQUENCE LISTING SUBMITTED ELECTRONICALLY

The content of the electronically submitted sequence listing (Name: 4662-4197_SEQ_LISTING.txt); Size: 6.34 Kilobytes; and Date of Creation: May 10, 2021) filed with the application is incorporated herein by reference in its entirety.

The present invention is related to an improved process for production of vitamin B2 using a genetically engineered host cell comprising a heterologous enzyme with pyridoxal phosphatase activity. Using said modified host cell, the yield of riboflavin production could be increased by at least about 5%.

Riboflavin is synthesized by all plants and many microorganisms but is not produced by higher animals. Riboflavin is essential for basic metabolism, because it is a precursor of coenzymes such as flavin adenine dinucleotide and flavin mononucleotide that are required in the enzymatic oxidation of carbohydrates. In higher animals, insufficient riboflavin supply can cause loss of hair, inflammation of the skin, vision deterioration, and growth failure.

Biosynthesis of riboflavin starts from guanosine triphosphate (GTP) and ribulose-5-phosphate. The genes involved in biosynthesis of riboflavin are known from various sources, such as e.g., *Bacillus subtilis, Ereothecium ashbyii, Ashbya gossypii, Candida flareri, Saccharomyces cerevisiae, E. coli* (see e.g. EP405370, FIG. 2 in EP1186664 or Ullman's Encyclopedia of Industrial Chemistry, 7th Edition, 2007, Chapter Vitamins).

The establishment of an industrial production process using microorganisms, such as e.g. strains of *Bacillus*, requires some modification of either the host strain and/or the process conditions (see e.g. Kil et al., Mol Gen Genet 233, 483-486, 1992; Mack et al., J. Bacteriol., 180:950-955, 1998). The metabolic flux into and through the riboflavin biosynthetic pathway has to be maintained at a high level by keeping the intracellular concentrations of ribulose-5-phophate above or as close as possible to the saturating substrate concentration of the 3,4-dihydroxy-2-butanone 4-phosphate synthase, a presumed rate limiting enzyme for the riboflavin biosynthetic pathway.

Transcription of the riboflavin operon from the rib promoter (Prib) is controlled by a riboswitch involving an untranslated regulatory leader region of almost 300 nucleotides located in the 5' region of the rib operon between the transcription start and the translation start codon of the first gene in the operon, ribG. Elongation of the nascent riboflavin RNA is dependent on the presence or absence of FMN or FAD: in the presence of these effectors, a transcription termination hairpin is formed (so-called rib terminator) wherein in their absence, the formation of a so-called anti-terminator results in read-through transcription of the rib operon.

Thus, the establishment of an industrial process using microorganisms involves a highly sophisticated multi-enzymatic process with several bottlenecks, such as e.g. the maintenance of an efficient direct metabolic flux throughout the whole process.

Surprisingly, we now found that a specific phosphatase known from the vitamin B6 biosynthetic pathway plays an important role in the fermentative production of riboflavin, leading to at least about 5% yield increase.

Particularly, the present invention is directed to a riboflavin-producing host cell, such as e.g. a (recombinant) host cell comprising (and expressing) riboflavin biosynthetic genes, particularly a riboflavin-producing *Bacillus*, comprising a heterologous enzyme with pyridoxal phosphatase [EC 3.1.3.74] activity.

According to the present invention, a riboflavin-producing host cell can be any suitable host cell which is capable of producing riboflavin, i.e. comprising (and expressing) riboflavin biosynthetic genes. Preferably, the riboflavin biosynthetic genes are from *Bacillus*, particularly from *Bacillus subtilis*, including e.g. riboflavin biosynthetic genes ribG (ribD), ribB (ribE), ribA, and ribH.

The heterologous enzyme with pyridoxal phosphatase [EC 3.1.3.74] activity present in the riboflavin-producing host cell as defined herein, might be obtainable from various sources, such as e.g. animals, plants, microorganisms including bacteria or fungi including yeast. In one embodiment the heterologous enzyme with the activity as defined herein is selected from a polypeptide with at least about 70%, such as e.g. 75, 80, 85, 90, 95, 98% or up to 100% identity to SEQ ID NO:2, which might be expressed by a polynucleotide according to SEQ ID NO:1.

The polypeptide according to SEQ ID NO:2 has been isolated from *Sinorhizobium meliloti* IFO 14782 (see UniProt accession no. A7BK78). Further sources for the polypeptide with at least 70% identity to SEQ ID NO:2 which could be used in a riboflavin-producing host cell as defined herein include but are not limited to strains of *Rhizobia*, such as e.g. *Sinorhizobium* sp. RAC02, *Sinorhizobium meliloti* strain USDA1021-ATCC 14580, *Rhizobium leguminosarum* (GenBank accession no. WP_018068721), *Sinorhizobium meliloti* BL225C; GenBank accession no. AEG03018.1) or the ones according to Table 4.

A riboflavin-producing host cell comprising riboflavin biosynthetic genes, such as e.g. a microorganism, in particular *Bacillus*, preferably *Bacillus subtilis*, comprising a heterologous enzyme as defined herein with pyridoxal phosphatase [EC 3.1.3.74] activity, particularly a heterologous enzyme/polypeptide with at least about 70% identity to SEQ ID NO:2, is referred herein as "modified" or "recombinant" host cell.

As used herein, a "non-modified" or "wild-type" riboflavin-producing host cell is a cell comprising riboflavin biosynthetic genes, such as e.g. a microorganism, particularly *Bacillus*, preferably *Bacillus subtilis*, but not comprising (expressing) an enzyme with the activity of the heterologous enzyme as defined herein.

As used herein, the term "heterologous enzyme" relates to an enzyme which is not an endogenous enzyme of the respective host cell, i.e. riboflavin-producing host cell. In order to be expressed in the host cell, the corresponding DNA encoding said enzyme has to be introduced into a suitable riboflavin-producing host cell, such as e.g. *Bacillus*. Thus, the present invention is related to a riboflavin-producing host cell, particularly *Bacillus*, preferably *B. subtilis*, wherein a polynucleotide encoding an enzyme with at least 70% identity to SEQ ID NO:2 having pyridoxal phosphatase

[EC 3.1.3.74] activity has been introduced and furthermore said polynucleotide being expressed (and active) in the host cell.

Introduction of a DNA sequence encoding such enzyme as defined herein may be for instance via addition or insertion of a DNA sequence by transformation, conjugation or transduction into the chromosome of a host cell or the DNA sequences might be introduced on replicative plasmid DNA, i.e. on a suitable expression vector. Said addition or insertion may occur by DNA recombination that may or may not also result in a removal or deletion of chromosomal DNA nucleotides. Methods by which introduction of DNA sequences into a host cell, e.g. microorganisms, are achieved, especially by site-specific introduction, are well-known in the art and described in e.g. Sambrook et al., 1989, Molecular Cloning, A Laboratory Manual, Cold Spring Harbor Press, N. Y.; and Ausubel et al. (eds.), 1995, Current Protocols in Molecular Biology, (John Wiley a Sons, N.Y.). The terms "modified" or "transformed" host cell might be used interchangeably herein. The skilled person knows the suitable methods and/or expression vectors to be used for generation of a modified host cell as defined herein.

According to an embodiment of the present invention, one or more copies of heterologous enzyme as defined herein, preferably a polypeptide with at least about 70% identity to SEQ ID NO:2 with pyridoxal phosphatase [EC 3.1.3.74] activity, such as e.g. a polypeptide encoded by a polynucleotide according to SEQ ID NO:1, might be introduced and expressed in the modified host cell as defined herein, such as e.g. 1, 2, 3, 4, 5 or more copies. The polynucleotide encoding the heterologous enzyme as defined herein and according to one aspect of the present invention might be under the control of a strong and/or constitutive or inducible promoter or might be further modified, such as e.g. through mutation of the gene encoding the heterologous enzyme or via introduction and/or genetically modifications of a transcriptional and/or translational regulator, including inactivation of transcriptional and/or translational inhibitors. These techniques are known to the skilled person.

Constitutive promoters useful for performance of the present invention include such as e.g. $P_{veg}$ associated with a prokaryotic ribosome binding site (RBS), such as the RBS of B. subtilis spoVG gene, e.g. nucleotides corresponding respectively to positions 1 to 46 of SEQ ID NO:3 (ATG-71 bp to ATG-26 bp) and to positions 55 to 71 of SEQ ID NO:3 (ATG-17 bp to ATG-1 bp). A further useful strong promoter is $P_{spo15}$. The introduction of such a strong promoter in a modified host cell as defined herein might result in an increase in riboflavin production which is at least 50%, 75%, 100%, 200%, 250%, 300%, 350%, 500% or even more than 1000% compared to using a non-modified host cell as defined herein. Thus, in one embodiment the heterologous enzyme as defined herein is used together with a specific promoter, including but not limited to $P_{veg}$ associated with an RBS.

In one embodiment, the modified host cell is capable of production of riboflavin wherein the yield of riboflavin is increased by at least about 5%, such as at least about 7, 8, 10, 15, 20, 30, 40, 50% or more, compared to a non-modified host cell.

In one embodiment, the activity of the (endogenous) ribC gene in the modified riboflavin-producing host cell as defined herein is reduced or abolished, in particular reduced by at least about 20%, preferably such as at least about 50, 60, 70, 80, 90%, most preferably wherein the ribC activity is abolished, i.e. reduced to zero activity. This might be achieved by e.g. knocking out the ribC gene or parts of the gene as described herein (see e.g. U.S. Pat. No. 5,837,528).

The skilled person knows how to genetically manipulate or modify such host cell e.g. resulting in reduction or abolishment of ribC activity. This includes, but is not limited to, e.g. gene replacement, gene amplification, gene disruption, transfection, transformation using plasmids, viruses, or other vectors.

Modifications in order to have the host cell produce less or no copies of the ribC gene and/or protein may include the use of a weak promoter, or the mutation (e.g. insertion, deletion or point mutation) of (parts of) the ribC gene (as described herein), in particular its regulatory elements. Furthermore, reduction or abolishment of ribC-specific activity might be achieved by contacting ribC with specific inhibitors or other substances that specifically interact with ribC. These methods which are known in the art could be used to generate a riboflavin-producing host cell wherein the activity of ribC is reduced or abolished and which comprises a heterologous polypeptide with pyridoxal phosphatase [EC 3.1.3.74] activity as described herein.

The modified host cell as defined herein might carry further modifications such as e.g. overexpression of one or more riboflavin biosynthetic gene(s), in particular ribA or introduction of multiple copies of the rib operon in the host cell, such as implemented in B. subtilis strain RB50 (see e.g. EP 405370). Compared to the riboflavin production in B. subtilis RB50, the riboflavin production can be increased by at least 100%, 200%, 250%, 500%, or even more than 750% by genetically altering a microorganism in such a way, i.e. via fusion of the rib genes to a strong promoter. According to one specific aspect of the present invention, a microorganism carrying a heterologous enzyme with pyridoxal phosphatase [EC 3.1.3.74] activity as defined herein optionally combined with the introduction of a strong promoter and/or multiple copy/copies of the rib operon may be furthermore altered via a decoupling of growth from production of riboflavin, such as e.g. via introduction of an auxotrophy such as described in EP1186664 for e.g. biotin, and/or furthermore combined with introduction of modified transketolase gene as e.g. described in WO2007051552, and/or furthermore combined with the use of modified rib leader sequences as e.g. described in WO2010052319.

A particular preferred strain according to the present invention which might be used as host for the production of riboflavin is B. subtilis. A more preferred strain is B. subtilis RB50:[pRF69]$_n$ containing multiple (n) copies (for example about 5 to about 20 copies) of pRF69 encoding a rib operon modified with the strong promoter $P_{spo15}$ to enhance transcription of the rib genes (see e.g. EP405370 and Perkins et al., J. Ind. Microbiol. Biotechnol., 22:8-18, 1999 for construction of the strain and culture conditions to result in riboflavin production).

The term "expression" includes any step involved in the production of the polypeptide including, but not limited to, transcription, post transcriptional modification, translation, post-translational modification, and secretion.

Sequence identity, or sequence homology are used interchangeable herein. In order to determine the percentage of sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/bases or amino acids. The sequence identity is the percentage of identical matches between the two sequences over the reported aligned region. The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P., Longden, I. and Bleasby, A. Trends in Genetics 16, (6) pp 276-277, emboss-.bioinformatics.nl/). For protein sequences EBLOSUM62 is used for the substitution matrix. For nucleotide sequences, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms. After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity as defined herein can be obtained from NEEDLE by using the NOBRIEF option and is labeled in the output of the program as "longest-identity".

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, word length=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25 (17): 3389-3402. When utilizing BLAST and Gapped BLAST programs, the default parameters of the respective programs (e.g., XBLAST and NBLAST) can be used. See the homepage of the National Center for Biotechnology Information at ncbi.nlm.nih.gov.

A "synthetic molecule" as described herein, such as a synthetic nucleic acid or a synthetic polypeptide is produced by in vitro chemical or enzymatic synthesis. It includes, but is not limited to, variant nucleic acids made with optimal codon usage for host organisms of choice.

A synthetic nucleic acid may be optimized for codon use, preferably according to the methods described in WO2006077258 and/or WO2008000632, including the method of codon-pair optimization. Codon-pair optimization is a method wherein the nucleotide sequences encoding a polypeptide that have been modified with respect to their codon-usage, in particular the codon-pairs that are used, are optimized to obtain improved expression of the nucleotide sequence encoding the polypeptide and/or improved production of the encoded polypeptide. Codon pairs are defined as a set of two subsequent triplets (codons) in a coding sequence. Those skilled in the art will know that the codon usage needs to be adapted depending on the host species, possibly resulting in variants with significant homology deviation from SEQ ID NO:2, but still encoding the polypeptide according to the invention. In one embodiment, the present invention is related to codon-optimized sequences to be heterologous expressed in the suitable riboflavin-producing host cell. An example of such codon-optimized sequence suitable for expression in *Bacillus subtilis* is shown in SEQ ID NO:4.

As used herein, the terms "variant" or "mutant" can be used interchangeably. They can refer to either polypeptides or polynucleotides. Variants include substitutions, insertions, deletions, truncations, transversions, and/or inversions, at one or more locations relative to a reference sequence. Variants can be made for example by site-saturation mutagenesis, scanning mutagenesis, insertional mutagenesis, random mutagenesis, site-directed mutagenesis, and directed-evolution, as well as various other recombination approaches known to a skilled person in the art. Variant genes of nucleic acids may be synthesized artificially by known techniques in the art.

As used herein, the term "specific activity" or "activity" with regards to enzymes means its catalytic activity, i.e. its ability to catalyze formation of a product from a given substrate. The specific activity defines the amount of substrate consumed and/or product produced in a given time period and per defined amount of protein at a defined temperature. Typically, specific activity is expressed in µmol substrate consumed or product formed per min per mg of protein. Typically, µmol/min is abbreviated by U (=unit). Therefore, the unit definitions for specific activity of µmol/min/(mg of protein) or U/(mg of protein) are used interchangeably throughout this document. An enzyme is active, if it performs its catalytic activity in vivo, i.e. within the host cell as defined herein or within a system in the presence of a suitable substrate. The skilled person knows how to measure enzyme activity, in particular activity of pyridoxal phosphatase or riboflavin biosynthetic enzymes as defined herein. Analytical methods to evaluate the capability of a suitable enzymes as defined herein including isolation and purification are known in the art.

Measurement of increase of pyridoxal phosphatase [EC 3.1.3.74] specific biological activity may be done as follows: prior to the genetic manipulation of the host cell, the— specific activity of said enzyme is measured and set as 100%. The same measurement is performed after modification/mutation of the host cell resulting in the heterologous enzyme-specific activity, i.e. an activity of more than 100%, which measurement is known in the art (as described in Sarge S, et al., Chembiochem. 2015 November; 16(17): 2466).

With regards to the present invention, it is understood that organisms, such as e.g. microorganisms, fungi, algae or plants also include synonyms or basonyms of such species having the same physiological properties, as defined by the International Code of Nomenclature of Prokaryotes or the International Code of Nomenclature for algae, fungi, and plants (Melbourne Code).

As used herein, the term "riboflavin" also includes riboflavin precursors, flavin mononucleotide (FMN), flavin adenine dinucleotide (FAD), and derivatives thereof. Riboflavin precursors and derivatives of riboflavin, FMN or FAD include but are not limited to: 2,5-diamino-6-ribosylamino-4

(3H)-pyrimidinone-5'-phosphate (DRAPP); 5-amino-6-ribosylamino-2,4 (1H,3H)-pyrinnidinedione-5'-phosphate; 2,5-diannino-6-ribitylannino-4 (3H)-pyrimidinone-5'-phosphate; 5-amino-6-ribitylamino-2,4 (1H,3H)-pyrinnidinedione-5'-phosphate; 5-amino-6-ribitylamino-2,4 (1H,3H)-pyrinnidinedione; 6,7-dimethyl-8-ribityllumazine (DMRL); and flavoproteins. Derivatives of riboflavin include but are not limited to: riboflavin-5-phosphate and salts thereof, such as e.g. sodium riboflavin-5-phosphate.

The terms "riboflavin" and "vitamin B2" are used interchangeably herein. The genes involved in biosynthesis of riboflavin as well as methods for fermentative production of riboflavin, in particular fermentative production using *Bacillus* strains, are known (see e.g. EP405370 or Ullman's Encyclopedia of Industrial Chemistry, 7th Edition, 2007, Chapter Vitamins). These methods may be also applied for production of riboflavin using modified host cells, particularly such as *Bacillus*, as described herein.

The present invention furthermore relates to a process for production of riboflavin, wherein a riboflavin-producing host cell, such as a modified host cell as defined herein, is incubated in an aqueous medium under conditions that allow the production of riboflavin from a given substrate. Using said modified host cell in a process for production of riboflavin, the yield can be increased by at least about 5%, such as e.g. at least about 7, 8, 10, 15, 20, 30, 40, 50% or more, compared to riboflavin produced with a non-modified host cell.

Several substrates may be used as a carbon source in a process of the present invention, i.e. a process for production of riboflavin as mentioned above. Particularly suited carbon sources may be selected from compounds consisting of 3, 5 or 6 carbon atoms, such as e.g. D-glucose, glycerol, thick juice, dextrose, starch, sucrose or ribose. Preferably, the carbon source is D-glucose. The term "carbon source", "substrate" and "production substrate" in connection with the above process is used interchangeably herein.

A medium as used herein for the above process using a modified host cell as defined herein may be any suitable medium for the production of riboflavin. Typically, the medium is an aqueous medium comprising for instance salts, substrate(s), and a certain pH. The medium in which the substrate is converted into riboflavin is also referred to as the production medium. An example of a suitable medium for production of riboflavin is described in WO2004113510 (VF-medium), which is particularly useful with regards to *Bacillus* and which might be used for the purpose of the present invention.

"Fermentation" or "production" or "fermentation process" as used herein may be the use of growing cells using media, conditions and procedures known to the skilled person, or the use of non-growing so-called resting cells, after they have been cultivated by using media, conditions and procedures known to the skilled person, under appropriate conditions for the conversion of suitable substrates into riboflavin.

The produced riboflavin may be recovered from the cells by any suitable means. Recovering means for instance that the produced riboflavin may be separated from the production medium. Optionally, the thus produced fermentation product may be further processed, e.g. purified.

In connection with the above process using a modified riboflavin-producing host cell as defined herein, in one aspect, the growing step can be performed in an aqueous medium, i.e. the growth medium, supplemented with appropriate nutrients for growth normally under aerobic conditions. The cultivation may be conducted, for instance, in batch, fed-batch, semi-continuous or continuous mode, wherein fed-batch or semi-continuous mode is preferred. Detailed fermentation methods are known to the skilled person or otherwise described in e.g. EP405370.

The cultivation period to be used for a process according to the present invention may vary depending on for instance the host, pH, temperature and nutrient medium to be used, and may be for instance about 10 h to about 10 days, preferably about 4 to about 7 days, more preferably about 2 to about 6 days, depending on the microorganism. The skilled person will know the optimal culture conditions of suitable microorganisms to be used in connection with the present invention.

The cultivation may be conducted for instance at a pH of about 7.0, preferably in the range of about 6 to about 8, more preferably about 6.5 to 7.5. A suitable temperature range for carrying out the cultivation may be for instance from about 13° C. to about 70° C., preferably from about 30° C. to about 39° C., more preferably from about 35° C. to about 39° C., and most preferably from about 36° C. to about 39° C. The culture medium for growth usually may contain such nutrients as assimilable carbon sources, e.g., D-glucose, glycerol, thick juice, dextrose, starch, sucrose or ribose; and digestible nitrogen sources such as organic substances, e.g., peptone, yeast extract and amino acids. The media may be with or without urea and/or corn steep liquor and/or baker's yeast. Various inorganic substances may also be used as nitrogen sources, e.g., nitrates and ammonium salts. Furthermore, the growth medium usually may contain inorganic salts, e.g., magnesium sulfate, manganese sulfate, potassium phosphate, and calcium carbonate. Cells obtained using the procedures described above can then be further incubated at essentially the same modes, temperature and pH conditions as described above, in the presence of substrates such as described above in such a way that they convert these substrates into the desired target fermentation product. Incubation can be conducted in a nitrogen-rich medium, containing, for example, organic nitrogen sources, e.g., peptone, yeast extract, baker's yeast, urea, amino acids, and corn steep liquor, or inorganic nitrogen sources, e.g., nitrates and ammonium salts, in which case cells will be able to further grow while producing the desired fermentation product. Alternatively, incubation can be conducted in a nitrogen-poor medium, in which case cells will not grow substantially, and will be in a resting cell mode, or biotransformation mode. In all cases, the incubation medium may also contain inorganic salts, e.g., magnesium sulfate, manganese sulfate, potassium phosphate, and calcium chloride. The skilled person will know which conditions to apply depending on the host cell.

The terms "production" or "productivity" are art-recognized and include the concentration of riboflavin formed within a given time and a given fermentation volume (e.g., kg product per hour per liter). The term "efficiency of production" includes the time required for a particular level of production to be achieved (for example, how long it takes for the cell to attain a particular rate of output of a fermentation product). The term "yield" is art-recognized and includes the efficiency of the conversion of the carbon source into the product (i.e., riboflavin). This is generally written as, for example, kg product per kg carbon source. By "increasing the yield and/or production/productivity" of the compound it is meant that the quantity of recovered molecules, or of useful recovered molecules of that compound in a given amount of culture over a given amount of time is increased.

Analytical methods for determining the yield/productivity of riboflavin are known in the art. Such methods may include but are not limited to HPLC or use of indicator strains (see e.g. Bretzel et al., J. Ind. Microbiol. Biotechnol. 22, 19-26, 1999).

The following examples are illustrative only and are not intended to limit the scope of the invention in any way. The contents of all references, patent applications, patents, and published patent applications, cited throughout this application, particularly EP405370, WO2007051552, U.S. Pat. No. 5,837,528, WO2006077258, WO2008000632, WO2017036903, WO2010052319, WO2004113510 and EP1186664 are hereby incorporated by reference.

EXAMPLES

Example 1: General Methods, Strains and Plasmids

Unless otherwise mentioned, all media and general methods are disclosed in WO2017036903. Genotyps of the used B. subtilis strains are listed in Table 1.

For isolation of plasmid DNA from B. subtilis the QIAprep Spin Miniprep Kit (Qiagen), following the manufacturer's recommendations, was used. Cells were harvested by centrifugation from a 10-ml culture in VY supplemented with ampicillin (100 µg/ml final) and incubated at 37° C., 250 rpm up to $OD_{600\ nm}$~0.8-1.2. The lysis buffer was supplemented with lysozyme (1 mg/ml f.c.) to degrade B. subtilis cell wall for 10 minutes at 37° C.

For amplification of DNA by PCR, 0.1 µg of chromosomal DNA from S. meliloti or B. subtilis was used in a 50 µl reaction volume containing 25 µl of 2× Phusion high-fidelity PCR master mix (New England Biolabs), 1 µl of the respective primers (Table 2). The PCR reaction was performed in 29 cycles of three sequential steps: (i) denaturing step at 95° C. for 30 sec; (ii) annealing step at 55° C. for 30 sec; (iii) elongation step at 72° C. for 1 min per kb. The PCR cycles were preceded by a denaturation step at 95° C. for 2 min.

For transduction of B. subtilis with SPP1 bacteriophage lysate, the donor lysate was prepared by inoculating a single colony of the donor strain in 3 ml VY medium. The culture was incubated overnight at 37° C. in a roller drum. The next day, 100 µl of the preculture was mixed with 100 µl of fresh VY and 30 µl of SPP1 bacteriophage lysate. After a 15-minute incubation at 37° C. in a water bath, 4 ml of fresh VY supplemented with $CaCl_2$ (5 mM final) were added. The infected culture was incubated during 4 hours at 37° C. in a roller drum. The lysed culture was centrifuged and the supernatant was filter-sterilized. The resulting donor lysate was stored at +4° C. for further use. The recipient strain was prepared by is inoculating a single colony of the donor strain in 3 ml VY medium. The culture was incubated overnight at 37° C. in a roller drum. The next day, 10 ml of fresh VY medium were inoculated with 500 µl of the preculture, and incubated at 37° C., 250 rpm up to $OD_{600\ nm}$~0.8-1.2. 900 µl of the culture were then infected with 10 or 100 µl of the donor lysate. 9 ml of fresh VY supplemented with $MgSO_4$ (10 mM final) were added to the culture. After a 30-minute incubation at 37° C. in a water bath, cells were harvested by centrifugation (10 min, 3500 rpm), suspended in 150 µl of 1×SS and spread on a selective agar medium, followed by incubation at 37° C. for 1 day.

Assay of riboflavin production in deep-well microtiter plates (MTP) was performed as follows: an overnight culture was made from a single colony in 3 ml of VY containing selective antibiotics where appropriate. The preculture was incubated at 39° C., 550 rpm, 80% humidity. The next day, 3 ml of RSM were inoculated with the preculture with a starting $OD_{600\ nm}$~0.05. Cultures in MTP were made in triplicate, covering the wells with a breath seal. MTP were incubated at 39° C., 550 rpm, 80% humidity for 48 hours. 250 µl of the 48 hour-culture were treated with 20 µl of 4M NaOH solution to solubilize the riboflavin crystals (shaken for 1 min at 300 rpm). 230 µl of a 1M potassium phosphate buffer, pH 6.8 were added (shaken for 1 min at 300 rpm). Riboflavin was assayed by HPLC using an Agilent 1100 series HPLC system with a quaternary pump, an autosampler, a UV detector and Fluorescence detector. The separation was achieved using a Supelcosil LC-8 DB (150 mm×4.6 mm×5 um). Optimal column temperature was 20° C. The mobile phase was a gradient from 100% 0.1M acetic acid to 50/50 0.1M acetic acid/methanol at 15 minutes for total of 33 minutes per run. The flow rate was 1.0 ml/min and the injection volume set to 5 µl. The UV signal was monitored and used for detection. Calibration range from 0.1 µg/ml to 500 µg/ml. Additionally, the potential accumulation of glucose in the culture broth was analyzed by a Waters HPLC system using a binary pump, an autosampler, a UV- and a refractive index detector. The separation was achieved on a CAPCELL PAK NH2 UG80 column (4.6 mm×250 mm, 5 µm; Shiseido). The optimal column temperature was 40° C. The mobile phase was a mixture of acetonitrile and deionized water at a ratio of 65:35. The flow rate was 1.0 ml/min and the injection volume set to 5 µl or 10 µl. The refractive index signal was monitored and used for detection. The calibration range for each compound was from 0.3 mg/ml to 3 mg/ml.

TABLE 1

Bacillus subtilis strains.

| Strain | Relevant genotype | Reference |
|---|---|---|
| BS168-SP1 | CIP106309 Trp+ | WO2017036903 |
| BS9645 | CIP106309 Trp+ pBHA12 E. coli/ B. subtilis shuttle vector | This patent |
| BS9646 | CIP106309 Trp+ pBV213L ($P_{amyQ}$_pdxP) | This patent |
| BS9502 | CIP106309 Trp+ amyE::Pveg_pdxP* | This patent |
| BS4905 | CIP106309 Trp+ Pspo15 triple ribO_del mro175rib ribC820 | WO2017036903 |
| BS8638 | CIP106309 Trp+ Pspo15_triple ribO_del mro175rib ribC820 amyE::Pveg_pdxP* | This patent |

Figure 1:
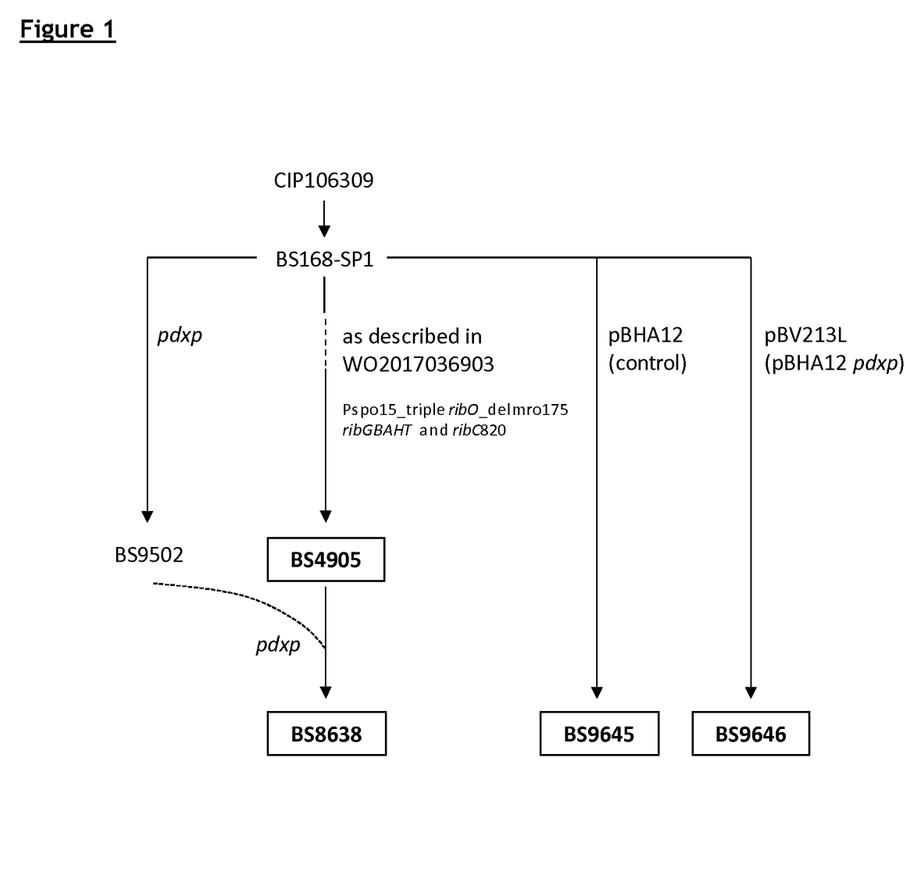
FIG. 1: Scheme of B. subtilis strain lineage.

Example 2: Cloning of Sinorhizobium meliloti pdxP in a Replicative Vector and Insertion in a Bacillus subtilis Host The pdxP gene from S. meliloti strain IFO14782 (SEQ ID NO:1) was amplified by PCR using primers P1 (SEQ ID NO:5) and P2 (SEQ ID NO:6). These oligos harbor BamHI (GGATTC) and NheI (GCTAGC) restriction sites, respectively. The resulting 0.8-kb fragment was purified by agarose gel electrophoresis and extracted from the gel using the QIAquick Gel Extraction Kit (Qiagen). The purified PCR product was cloned at the BamHI and NheI in the multiple cloning site of the pBHA12 *E. coli/B. subtilis* shuttle vector described in WO2008000632. This vector allows the expression of pdxP gene under the control of a promoter derived from the amyQ gene of *Bacillus amyloliquefaciens*. During the procedure of cloning and transformation of *B. subtilis*, *E. coli* was used as an intermediate host. The transformation of the ligation mixture was first performed in TOP10 Chemically Competent *E. coli* (Invitrogen). Several *E. coli* ampicillin-resistant colonies were isolated and the recombinant plasmid pBV213L (see FIG. 1) was extracted using the QIAprep Spin Miniprep Kit (Qiagen). The strain *Bacillus subtilis* BS168-SP1 is a tryptophan-prototroph derivative of the Marburg strain 168 (Germany) that was generated by replacing trpC2 mutation by a non-mutated trpC gene from strain *B. subtilis* ATCC 6051. Construction of BS168-SP1 is detailed in WO2017036903. BS168-SP1 is a naive strain with respect to riboflavin overproduction. In the next step, 10 µl of plasmid pBHA12 (WO2008000632) or 10 µl of plasmid pBV213L were transformed in strain BS168-SP1 by competent cell transformation, selecting for kanamycin-resistant clones (10 µg/ml f.c.) on TBAB plates. The resulting strains BS9645 and BS9646 were confirmed to harbor respectively the empty vector pBHA12 (BS9645) or the recombinant vector pBV213L with *S. meliloti* pdxP gene (BS9646). Nucleotide sequences showing the start codon of the coding sequences are listed in Table 2, with reference to the SEQ ID NO:s in the sequence listing.

TABLE 2

Nucleotide sequences of pdxP as isolated from *S. Meliloti* and as codon-optimized for expression in *B. subtilis* (pdxP*). The start codon of the coding sequence is underlined. For more details, see text and sequence listing.

| Name | Sequence 5' to 3' | SEQ ID NO: |
|---|---|---|
| pdxP | ATGGCCAATCGGGTCGCAGGTGAACAAACCGTTTTGCTTCGCAAG CCGGCCGTGTCATAAACCCGCCCATGAAGAAGCTCGACCGCATGC CGACCCACGCCGAATTCGCCCATGTCACCGACTGGGTCTTCGACC TCGACAACACGCTCTATCCGCATCACGTCAATCTGTTCTCACAGA TCGACCGCAACATGACGGCCTATGTTGCCGAACTCCTGTCGCTGG AGCCTGCGGAGGCGAAGAAGCTGCAGAAGGAATACTACCGCGACC ACGGCACCACGCTTCAGGGCCTGATGCTTCATCACGGCATCGATC CCAATGATTTCCTCGAAAGAGCCCACGCCATCGACTATAGCGTGG TGCCGGCCGATCCGGCGCTCGGCGAGGCGATCAAGGCGCTGCCCG GACGCAAGTTCATCTTCACCAACGGCAGCGTCGCCCATGCGGAGA TGACCGCGCGGGCGCTCGGCATTCTCGAGCATTTCAACGACATCT TCGACATCGTCGCCGCCGGCTTCATACCGAAGCCCGCCGGCGACA CCTACGACAAGTTCATGGGCCTTCACCGCATCGACACGGCGAATG CGGTGATGTTCGAGGATCTGCCGCGCAACCTGGTCGTCCCTAAGG CGCTCGGCATGAAGACGGTGCTGCTCGTGCCGCGCAATCTCGAAT ACGAGTTCGCCGAGGCCTGGGAAACGTCGAGCGACGCGGACGATC AGATCGACTACGTCACGGAAGACCTGGCGGGTTTCCTGCGCAGTG TGATTGTTTAA | 1 |
| Pveg; spoVG RBS | TTAAATTTTATTTGACAAAAATGGGCTCGTGTTGTACAATAAATG TTACTAGAGAAAGGTGGTGAACTACTATG | 3 |
| pdxP* | ATGGCTAATCGTGTGGCGGGTGAACAGACGGTGCTGCTGCGGAAA GCGGGTCGGGTGATCAATCCTCCTATGAAAAAACTGGACAGAATG CCGACACATGCTGAATTTGCCCATGTTACAGATTGGGTGTTTGAT CTGGATAACACACTGTATCCGCATCATGTCAACTTATTTTCTCAA ATCGATAGAAACATGACAGCATACGTTGCGGAACTGCTTTCATTA GAACCGGCTGAAGCCAAAAAACTGCAAAAAGAATACTACAGAGAT CATGGCACAACACTGCAGGGACTTATGTTACATCATGGAATTGAT CCGAACGATTTTCTTGAACGCGCACATGCGATCGATTATTCTGTG GTGCCTGCTGATCCGGCACTGGGAGAAGCAATTAAAGCGCTTCCG GGAAGAAAATTTATCTTTACAAACGGCTCTGTGGCTCATGCCGAA ATGACAGCACGCGCGCTGGGCATTCTTGAACATTTTAACGATATC TTTGATATCGTCGCAGCGGGCTTTATCCCGAAACCGGCAGGAGAT ACATACGATAAATTTATGGGACTTCATAGAATCGATACAGCTAAC GCCGTTATGTTTGAAGATCTTCCGCGCAATTTAGTCGTTCCGAAA GCTCTTGGCATGAAAACAGTGTTACTGGTCCCGCGCAATTTAGAA TATGAATTTGCAGAAGCGTGGGAAACATCAAGCGATGCCGACGAC CAGATTGACTACGTTACGGAAGACTTGGCAGGCTTTTTACGGAGC GTGATTGTTTAA | 4 |

Example 3: Insertion of *S. meliloti* pdxP in the Chromosome of a Riboflavin-Overproducing *B. subtilis* Host A codon-optimized pdxP gene (SEQ ID NO:4)—encoding the same protein as the native gene—was inserted in the amyE locus in the chromosome of BS168-SP1 recipient strain. A splicing by overhang extension (SOEing) PCR was used to generate a DNA fragment bearing the pdxP* gene, flanked by amyE-5' and the amyE-3' DNA sequences that allows the stable insertion in BS168-SP1 chromosome by double crossing-over. A genetic module harboring a chloramphenicol acetyltransferase (E.0 2.3.1.28) gene, that provides an antibiotics resistance to chloramphenicol, was also inserted between the amy-E3' flank and the pdxP* gene, in opposite orientation to pdxP*. First, individual PCRs were performed to amplify: (i) the 1.9 kb-DNA region that bears the amyE-3' flank and the chloramphenicol cassette, from pDG1662 plasmid (*Bacillus Genetic Stock Center, The Ohio State University, USA; GenBank U46197*) using primer pair P3 (SEQ ID NO:7) and P4 (SEQ ID NO:8); (ii) the 0.9 kb-DNA region that bears the pdxP* gene using primer pair P5 (SEQ ID NO:9) and P6 (SEQ ID NO:10). The *S. meliloti* IFO14782 pdxP* coding sequence (SEQ ID NO:4), which expression is driven by *B. subtilis* veg promoter and *B. subtilis* spoVG RBS (SEQ ID NO:3), was made synthetically and cloned in vector pJET1.2 (Thermo Fisher Scientific) by Genscript, Piscataway, NJ, USA. This recombinant vector was used as a template for the PCR; (iii) the 0.5 kb-DNA region that bears the amyE-5' flank from pDG1662 plasmid using primer pair P7 (SEQ ID NO:11) and P8 (SEQ ID NO:12). The three PCR products were separated by agarose gel electrophoresis and extracted from the gel using the QIAquick Gel Extraction Kit (Qiagen). Thanks to the overlapping DNA regions, they were assembled in a 3.2 kb-SOEing PCR fragment, using primer pair P3 and P8. The resulting SOEing PCR product was purified by agarose gel electrophoresis and extracted from the gel using the QIAquick Gel Extraction Kit (Qiagen). 1 µg was then used for the transformation of competent *B. subtilis* BS168-SP1. Chloramphenicol-resistant (CmR) colonies were selected on TBAB plates containing chloramphenicol 5 µg/ml. The insertion of pdxP* in the chromosomal amyE gene (alpha-amylase) of BS168-SP1 was confirmed by a starch hydrolysis test using iodine stain. The correct genotype of the resulting strain BS9502 was also confirmed by a PCR. Insertion of pdxP* gene in the chromosomal amyE locus of the *B. subtilis* riboflavin overproducing strain BS4905 (described in WO2017036903) was then performed with SPP1 phage according to the method described above, wherein a lysate of BS9502 was used to transduce the strain *B. subtilis* BS4905. CmR colonies were selected on TBAB plates containing 5 µg/ml chloramphenicol. The insertion of pdxP* in the chromosomal amyE gene (alpha-amylase) of BS168-SP1 was confirmed by a starch hydrolysis test using iodine stain. The correct genotype of the resulting strain BS8638 was also confirmed by PCR.

Example 4: Riboflavin Production Assay in Presence/Absence of pdxP Gene

The pdxP gene is overexpressed on a replicative vector in strain BS9646 (see Ex. 2) and via chromosomal insertion in strain BS8638 (see Ex. 3). Assay of riboflavin production was made from a culture with RSM in deep-well microtiter plates, as described above. The results are shown in Table 3.

TABLE 3

Riboflavin production with various *B. subtilis* strains having different genotypes as indicated. Strains *B. subtilis* BS9645 and BS9646 share the same genotype background (except for pdxP insertion), strains *B. subtilis* BS4905 and BS8638 share the same genotype background (except for pdxP insertion). For more explanation see text.

| Strain | Relevant genotype | Riboflavin Yield (g/100 g Glucose) |
|---|---|---|
| BS168-SP1 | wild-type | <0.003 |
| BS9645 | pBHA12 | <0.003 |
| BS9646 | pBV213L (pBHA12 with Pveg_pdxP) | 0.54 |
| BS4905 | riboflavin overproducer | 6.21 |
| BS8638 | riboflavin overproducer with Pveg_pdxP | 7.11 |

Figure 2:
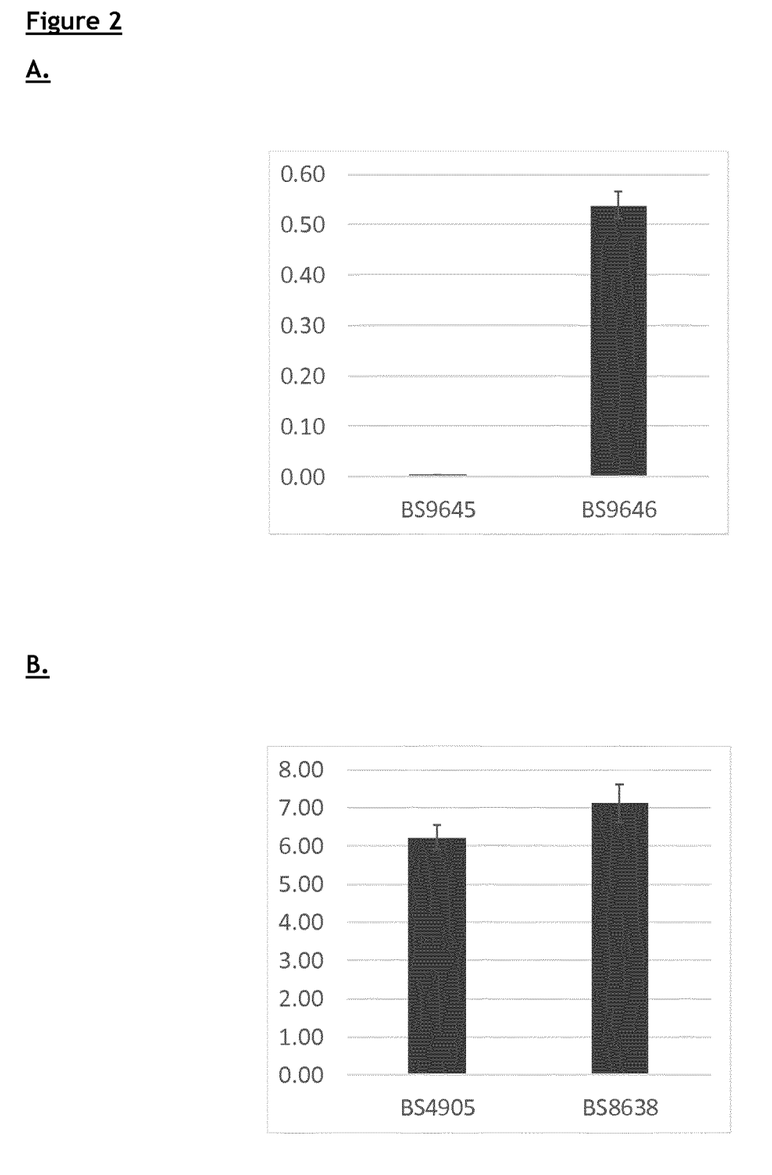
FIG. 2: Riboflavin production yields in % (y-axis) in the presence (i.e. BS9646 or BS8638) or absence (BS9645 or BS4905) of pdxP gene. For more details, see Example 4 (Table 3).

The riboflavin production yield of BS9646 was improved by at least 18000% compared to its direct parent BS9645 (see FIG. 2A). As no riboflavin can be detected in the culture of BS9645, BS9646 was compared to the detection limit of our HPLC riboflavin assay (0.003 g/100 g glucose). Performing the experiments in a riboflavin-overproducing strain background, the riboflavin production yield was improved by 14.5% compared to its direct parent (BS8638 compared with BS4902 (see Table 3 and FIG. 2B). These results showed a positive impact of the pdxP gene expression on the riboflavin production, in both a wild-type based strain (non-overproducing strain background) and in riboflavin overproducing strain background of *B. subtilis*.

Example 5: Identification and Cloning of pdxP Homologues

A homology search using the PdxP from *S. meliloti* revealed several pdxP homologues from other *Rhizobium* strains (see Table 4).

TABLE 4

Homology (% identity) of PdxP protein sequence within various *Rhizobium* species.

| Rhizobium species | % identity |
|---|---|
| *Sinorhizobium meliloti* sp. | 97-100% |
| *Sinorhizobium medicae* | 95% |
| *Sinorhizobium saheli* | 91% |
| *Sinorhizobium americanum* sp. | 90-91% |
| *Sinorhizobium fredii* sp. | 89-90% |
| *Rhizobium arenae* | 86% |
| *Pararhizobium polinicum* | 84% |
| *Rhizobium oryzae* | 78% |
| *Rhizobium leguminosarum* | 74% |

The homologs are cloned into a riboflavin-producing host, such as e.g. *B. subtilis*, as described above followed by a riboflavin production assay as described in Example 4.

When using the pdxP-homologs, the yield of riboflavin can be increased in the range of at least 5 to 20% in a riboflavin-overproducing strain background, i.e. equivalent to the numbers shown in Table 3.

The invention claimed is:

1. A riboflavin-producing *Bacillus subtilis* host cell expressing a polynucleotide encoding a heterologous enzyme with pyridoxal phosphatase activity, wherein the heterologous enzyme comprises a polypeptide with at least 95% sequence identity to the polypeptide of SEQ ID NO:2, and wherein the host cell comprises a mutation in an endogenous ribC gene that disrupts the expression of the endogenous ribC gene.

2. The riboflavin-producing host cell according to claim 1, wherein the heterologous enzyme is a *Sinorhizobium meliloti* enzyme.

3. The riboflavin-producing host cell according to claim 1, wherein the yield of riboflavin is increased by at least 5% from a given carbon source compared to the yield of riboflavin using the corresponding host cell not expressing the polynucleotide encoding the heterologous enzyme.

4. The riboflavin-producing host cell according to claim 1, wherein the heterologous enzyme comprises a polypeptide with at least 98% sequence identity to the polypeptide of SEQ ID NO: 2.

5. A process for production of riboflavin, comprising
(a) incubating a riboflavin-producing microbial host cell in an aqueous medium under conditions that allow the production of riboflavin from a given substrate; and
(b) isolating the riboflavin from the cultivation medium, wherein the riboflavin-producing host cell expresses a polynucleotide encoding a heterologous enzyme with pyridoxal phosphatase activity, wherein the heterologous enzyme comprises a polypeptide with at least 95% sequence identity to the polypeptide of SEQ ID NO:2.

6. The process according to claim 5, wherein the yield of riboflavin is increased by at least 5% compared to a process using the corresponding host cell that does not express the heterologous enzyme.

7. The process according to claim 5 further comprising the step of isolating and purifying the riboflavin from the cultivation medium.

8. The process according to claim 5, wherein the host cell is selected from the group consisting of *Bacillus subtilis, Bacillus cereus, Bacillus amyloliquefaciens, Bacillus stearothermophilus, Bacillus halodurans, Bacillus licheniformis, Streptococcus aureus, Streptococcus pneumoniae, Clostridium acetobutylicum, Clostridium difficile, Lactococcus lactis, Streptomyces coelicolor, Corynebacterium diphteriae* and *Corynebacterium glutamicum*.

9. The process according to claim 5, wherein the host cell is *Bacillus subtilis*.

10. The process according to claim 9, wherein the host cell comprises a mutation in an endogenous ribC gene that disrupts the expression of the endogenous ribC gene.

11. The process according to claim 5, wherein the heterologous enzyme is a *Sinorhizobium meliloti* enzyme.

12. The process according to claim 5, wherein the heterologous enzyme comprises a polypeptide with at least 98% sequence identity to the polypeptide of SEQ ID NO: 2.

* * * * *

SEQUENCE LISTING

<160> NUMBER OF SEQ ID NOS: 12

<210> SEQ ID NO 1
<211> LENGTH: 776
<212> TYPE: DNA
<213> ORGANISM: Sinorhizobium meliloti

<400> SEQUENCE: 1

```
atggccaatc gggtcgcagg tgaacaaacc gttttgcttc gcaagccggc cgtgtcataa      60
acccgcccat gaagaagctc gaccgcatgc cgacccacgc cgaattcgcc catgtcaccg     120
actgggtctt cgacctcgac aacacgctct atccgcatca cgtcaatctg ttctcacaga     180
tcgaccgcaa catgacggcc tatgttgccg aactcctgtc gctggagcct gcggaggcga     240
agaagctgca gaaggaatac taccgcgacc acggcaccac gcttcagggc ctgatgcttc     300
atcacggcat cgatcccaat gatttcctcg aaagagccca cgccatcgac tatagcgtgg     360
tgccggccga tccggcgctc ggcgaggcga tcaaggcgct gcccgacgc aagttcatct     420
tcaccaacgg cagcgtcgcc catgcggaga tgaccgcgcg ggcgctcggc attctcgagc     480
atttcaacga catcttcgac atcgtcgccg ccggcttcat accgaagccc gccggcgaca     540
cctacgacaa gttcatgggc cttaccgca tcgacacggc gaatgcggtg atgttcgagg     600
atctgccgcg caacctggtc gtccctaagg cgctcggcat gaagacggtg ctgctcgtgc     660
cgcgcaatct cgaatacgag ttcgccgagg cctgggaaac gtcgagcgac gcggacgatc     720
agatcgacta cgtcacggaa gacctggcgg gtttcctgcg cagtgtgatt gtttaa        776
```

<210> SEQ ID NO 2
<211> LENGTH: 258
<212> TYPE: PRT
<213> ORGANISM: Sinorhizobium meliloti

<400> SEQUENCE: 2

```
Met Ala Asn Arg Val Ala Gly Glu Gln Thr Val Leu Leu Arg Lys Ala
1               5                   10                  15

Gly Arg Val Ile Asn Pro Pro Met Lys Lys Leu Asp Arg Met Pro Thr
            20                  25                  30

His Ala Glu Phe Ala His Val Thr Asp Trp Val Phe Asp Leu Asp Asn
        35                  40                  45

Thr Leu Tyr Pro His His Val Asn Leu Phe Ser Gln Ile Asp Arg Asn
    50                  55                  60

Met Thr Ala Tyr Val Ala Glu Leu Leu Ser Leu Glu Pro Ala Glu Ala
65                  70                  75                  80

Lys Lys Leu Gln Lys Glu Tyr Tyr Arg Asp His Gly Thr Thr Leu Gln
                85                  90                  95

Gly Leu Met Leu His His Gly Ile Asp Pro Asn Asp Phe Leu Glu Arg
            100                 105                 110

Ala His Ala Ile Asp Tyr Ser Val Val Pro Ala Asp Pro Ala Leu Gly
        115                 120                 125

Glu Ala Ile Lys Ala Leu Pro Gly Arg Lys Phe Ile Phe Thr Asn Gly
    130                 135                 140

Ser Val Ala His Ala Glu Met Thr Ala Arg Ala Leu Gly Ile Leu Glu
145                 150                 155                 160

His Phe Asn Asp Ile Phe Asp Ile Val Ala Ala Gly Phe Ile Pro Lys
                165                 170                 175

Pro Ala Gly Asp Thr Tyr Asp Lys Phe Met Gly Leu His Arg Ile Asp
            180                 185                 190
```

```
        Thr Ala Asn Ala Val Met Phe Glu Asp Leu Pro Arg Asn Leu Val Val
                195                 200                 205

Pro Lys Ala Leu Gly Met Lys Thr Val Leu Leu Val Pro Arg Asn Leu
            210                 215                 220

Glu Tyr Glu Phe Ala Glu Ala Trp Glu Thr Ser Ser Asp Ala Asp Asp
        225                 230                 235                 240

Gln Ile Asp Tyr Val Thr Glu Asp Leu Ala Gly Phe Leu Arg Ser Val
                        245                 250                 255

Ile Val

<210> SEQ ID NO 3
<211> LENGTH: 74
<212> TYPE: DNA
<213> ORGANISM: Artificial Sequence
<220> FEATURE:
<223> OTHER INFORMATION: promoter

<400> SEQUENCE: 3
ttaaatttta tttgacaaaa atgggctcgt gttgtacaat aaatgttact agagaaaggt      60
ggtgaactac tatg                                                       74

<210> SEQ ID NO 4
<211> LENGTH: 777
<212> TYPE: DNA
<213> ORGANISM: Artificial Sequence
<220> FEATURE:
<223> OTHER INFORMATION: pdxP codon-opt

<400> SEQUENCE: 4
atggctaatc gtgtggcggg tgaacagacg gtgctgctgc ggaaagcggg tcgggtgatc      60
aatcctccta tgaaaaaact ggacagaatg ccgacacatg ctgaatttgc ccatgttaca     120
gattgggtgt tgatctgga taacacactg tatccgcatc atgtcaactt attttctcaa     180
atcgatagaa acatgacagc atacgttgcg gaactgcttt cattagaacc ggctgaagcc     240
aaaaaactgc aaaagaata ctacagagat catggcacaa cactgcaggg acttatgtta     300
catcatggaa ttgatccgaa cgattttctt gaacgcgcac atgcgatcga ttattctgtg     360
gtgcctgctg atccggcact gggagaagca attaaagcgc ttccgggaag aaaatttatc     420
tttacaaacg gctctgtggc tcatgccgaa atgacagcac gcgcgctggg cattcttgaa     480 catttaacg atatctttga tatcgtcgca gcgggcttta tcccgaaacc ggcaggagat     540
acatacgata aatttatggg acttcataga atcgatacag ctaacgccgt tatgtttgaa     600
gatcttccgc gcaatttagt cgttccgaaa gctcttggca tgaaaacagt gttactggtc     660
ccgcgcaatt tagaatatga atttgcagaa gcgtgggaaa catcaagcga tgccgacgac     720
cagattgact acgttacgga agacttggca ggcttttac ggagcgtgat tgtttaa        777

<210> SEQ ID NO 5
<211> LENGTH: 46
<212> TYPE: DNA
<213> ORGANISM: Artificial Sequence
<220> FEATURE:
<223> OTHER INFORMATION: primer

<400> SEQUENCE: 5
gcatggatcc agaaaggagg tgatccaatg gccaatcggg tcgcag                     46

<210> SEQ ID NO 6
```

```
<211> LENGTH: 37
<212> TYPE: DNA
<213> ORGANISM: Artificial Sequence
<220> FEATURE:
<223> OTHER INFORMATION: primer

<400> SEQUENCE: 6
gcatgctagc attaaacaat cacactgcgc aggaaac                        37

<210> SEQ ID NO 7
<211> LENGTH: 23
<212> TYPE: DNA
<213> ORGANISM: Artificial Sequence
<220> FEATURE:
<223> OTHER INFORMATION: primer

<400> SEQUENCE: 7
gcacgcaagg taatcgtcag ttg                                       23

<210> SEQ ID NO 8
<211> LENGTH: 48
<212> TYPE: DNA
<213> ORGANISM: Artificial Sequence
<220> FEATURE:
<223> OTHER INFORMATION: primer

<400> SEQUENCE: 8
ccatttttgt caaataaaat ttaaaagctt atcgaattct catgtttg             48

<210> SEQ ID NO 9
<211> LENGTH: 48
<212> TYPE: DNA
<213> ORGANISM: Artificial Sequence
<220> FEATURE:
<223> OTHER INFORMATION: primer

<400> SEQUENCE: 9
caaacatgag aattcgataa gcttttaaat tttatttgac aaaaatgg             48

<210> SEQ ID NO 10
<211> LENGTH: 46
<212> TYPE: DNA
<213> ORGANISM: Artificial Sequence
<220> FEATURE:
<223> OTHER INFORMATION: primer

<400> SEQUENCE: 10
cacaaattaa aaactggtct gatcggatcc ttaaacaatc acgctc               46

<210> SEQ ID NO 11
<211> LENGTH: 46
<212> TYPE: DNA
<213> ORGANISM: Artificial Sequence
<220> FEATURE:
<223> OTHER INFORMATION: primer

<400> SEQUENCE: 11
gagcgtgatt gtttaaggat ccgatcagac cagttttta tttgtg               46
```

```
<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
gcggctgcga gtgctgaaac                                                 20
```